(12) United States Patent
Soni

(10) Patent No.: US 12,721,506 B2
(45) Date of Patent: Sep. 1, 2026

(54) MEDICAL SCOPE

(71) Applicant: Samit Soni, Houston, TX (US)

(72) Inventor: Samit Soni, Houston, TX (US)

( * ) Notice: Subject to any disclaimer, the term of this patent is extended or adjusted under 35 U.S.C. 154(b) by 314 days.

(21) Appl. No.: 18/585,984

(22) Filed: Feb. 23, 2024

(65) Prior Publication Data

US 2025/0268463 A1 Aug. 28, 2025

(51) Int. Cl.

| | |
|---|---|
| ***A61B 1/015*** | (2006.01) |
| ***A61B 1/00*** | (2006.01) |
| ***A61B 1/005*** | (2006.01) |
| ***A61B 1/018*** | (2006.01) |
| ***A61B 1/06*** | (2006.01) |
| ***A61B 1/273*** | (2006.01) |
| ***A61B 1/307*** | (2006.01) |

(52) U.S. Cl.

CPC .......... *A61B 1/015* (2013.01); *A61B 1/00009* (2013.01); *A61B 1/00016* (2013.01); *A61B 1/0002* (2013.01); *A61B 1/00029* (2013.01); *A61B 1/00066* (2013.01); *A61B 1/00108* (2013.01); *A61B 1/0052* (2013.01); *A61B 1/0057* (2013.01); *A61B 1/018* (2013.01); *A61B 1/0676* (2013.01); *A61B 1/2733* (2013.01); *A61B 1/307* (2013.01)

(58) Field of Classification Search

CPC ... A61B 1/00016; A61B 1/015; A61B 1/0002; A61B 1/00108; A61B 1/0052; A61B 1/0057

See application file for complete search history.

(56) References Cited

U.S. PATENT DOCUMENTS

2003/0032862 A1* 2/2003 Ota ........................ A61B 1/015 600/158
2005/0119527 A1* 6/2005 Banik ................ A61B 1/00066 600/117
2012/0302829 A1* 11/2012 Omoto .................. A61B 1/015 600/109
2013/0096382 A1* 4/2013 Alexander ............ A61B 1/005 600/110

* cited by examiner

*Primary Examiner* — Aaron B Fairchild
(74) *Attorney, Agent, or Firm* — The Rapacke Law Group, P.A.

(57) ABSTRACT

A medical scope that includes a handheld controller comprising an elongate controller housing sized to be operable by one hand of a user; a fluid reservoir positioned within the elongate controller housing and including a fluid cavity in fluid communication with at least one irrigation channel positioned inside an insertion tube; a fluid pump in operative communication with a second control and in fluid communication with the fluid cavity and the irrigation channel; a camera positioned at an first end portion of the insertion tube; memory, an antenna, and a processor positioned within the elongate controller housing, wherein the processor is in operative communication with at least the memory, the camera, and the antenna, wherein the processor is configured at least to: receive image data from the camera; and wirelessly send, through the antenna, the image data to a computing device located within a predetermined distance from the antenna.

20 Claims, 17 Drawing Sheets

70
156
14

MEDICAL SCOPE

TECHNICAL FIELD

The embodiments generally relate to the field of medical scopes.

BACKGROUND

Medical scopes such as endoscopes or cystoscopes can typically be physically connected, via a fluid tube, to a separate fluid reservoir bag that is suspended by a stand. Such medical scopes are also commonly physically connected to one or more computers via electrical cables for communicating images of the human body to the one or more computers. However, these physical connections can be obstructive during medical procedures.

There is a need for a medical scope that does not require to be physically connected to external devices or components.

SUMMARY

This summary is provided to introduce a variety of concepts in a simplified form that is further disclosed in the detailed description of the embodiments. This summary is not intended to identify key or essential inventive concepts of the claimed subject matter, nor is it intended for determining the scope of the claimed subject matter.

In general, the disclosed medical scope can include a handheld controller constructed and arranged to be operated in a one hand mode of operation and in a two hand mode of operation, the handheld controller including: an elongate controller housing sized to be operable by one hand of a user; a first control proximate to a first side of the elongate controller housing; a second control proximate to a second side opposite the first side of the elongate controller housing; an insertion tube constructed and arranged to be connected to the elongate controller housing, wherein at least a first end portion of the insertion tube is constructed and arranged to be deflected; one or more cables or wires positioned within the insertion tube, the one or more cables or wires being constructed and arranged to connect at least the first control to the first end portion of the insertion tube, wherein during the one hand mode of operation the first control is positioned so as to be actuated by one thumb of the user to tension at least a first cable or wire of the one or more cables or wires to deflect at least the first end portion of the insertion tube; one or more irrigation channels positioned within the insertion tube, the one or more irrigation channels being constructed and arranged to extend at least from inside the housing to the first end portion of the insertion tube; a fluid reservoir positioned within the elongate controller housing and including a fluid cavity that is constructed and arranged to be in fluid communication with at least a first irrigation channel of the one or more irrigation channels positioned inside the insertion tube; one or more fluid pumps in operative communication with the second control and constructed and arranged to be in fluid communication with the fluid cavity, the one or more fluid pumps being constructed and arranged to pump fluid from the fluid reservoir and into the one or more irrigation channels, wherein during the one hand mode of operation the second control is positioned so as to be actuated by one or more fingers of the user to activate the one or more fluid pumps; one or more cameras positioned at the first end portion of the insertion tube; memory positioned within the elongate controller housing; one or more antennas positioned within the elongate controller housing; one or more processors positioned within the elongate controller housing, wherein the one or more processors are in operative communication with at least the memory, the one or more cameras, and the one or more antennas, wherein the one or more processors are configured at least to: receive image data and/or video data from the one or more cameras; and wirelessly send, through the one or more antennas, the image data and/or video data to a computing device located within a predetermined distance from the one or more antennas.

Other illustrative variations within the scope of the invention will become apparent from the detailed description provided hereinafter. The detailed description and enumerated variations, while disclosing optional variations, are intended for purposes of illustration only and are not intended to limit the scope of the invention.

BRIEF DESCRIPTION OF THE DRAWINGS

A more complete understanding of the embodiments, and the attendant advantages and features thereof, will be more readily understood by references to the following detailed description when considered in conjunction with the accompanying drawings wherein.

Figure 1:
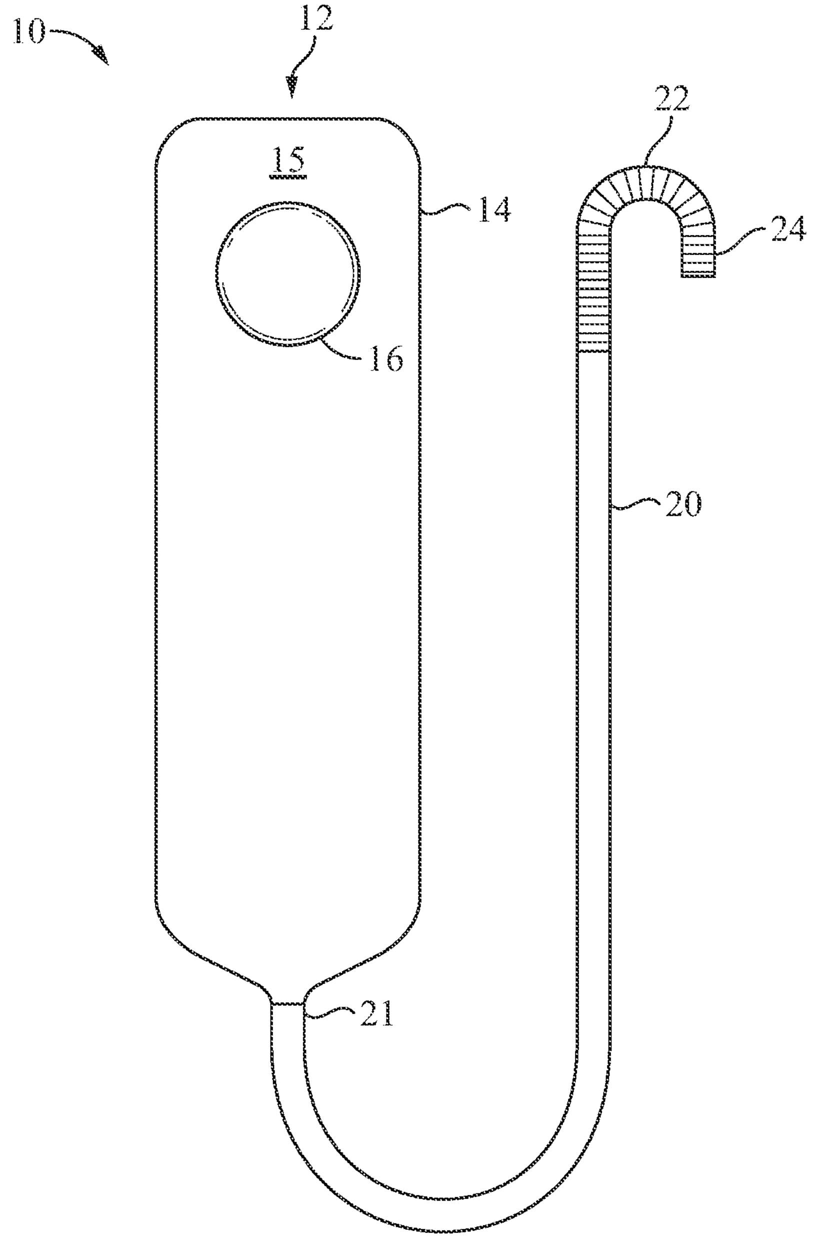
FIG. 1 illustrates a medical scope, according to some embodiments disclosed herein.

The drawings are not necessarily to scale, and certain features and certain views of the drawings may be shown exaggerated in scale or in schematic in the interest of clarity and conciseness.

DETAILED DESCRIPTION

The specific details of the single embodiment or variety of embodiments described herein are to the described product or methods of use. Any specific details of the embodiments are used for demonstration purposes only and no unnecessary limitations or inferences are to be understood from there.

It is noted that the embodiments reside primarily in combinations of components and procedures related to the products. Accordingly, the product and components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

In general, the embodiments described herein relate to a medical scope that is constructed to be handheld and configured to wirelessly connect to a computing device. In some embodiments, the medical scope can include a handheld controller constructed and arranged to be operated in a one hand mode of operation and in a two hand mode of operation. The handheld controller can include an elongate controller housing sized to be operable by one hand of a user, and one or more controls for operating the medical scope. The handheld controller can be made primarily of any suitable durable material such as, for example, plastic, metal, wood, or any combination thereof.

In some embodiments, the medical scope can be an endoscope. In some embodiments, the medical scope can be a cystoscope, bronchoscope, a hysteroscope, a vaginoscope, or a colonoscope. In some embodiments, the medical scope can include an insertion tube constructed and arranged to be connected to the elongate controller housing. In some embodiments, the insertion tube can be constructed and arranged to be inserted into any cavity or orifice of the human body. In some embodiments, the insertion tube can be flexible. For example, the insertion tube can include an articulated portion that is constructed and arranged to be deflected. In some embodiments, the insertion tube can be rigid. For example the insertion tube can include a rigid portion that is constructed and arranged not to be deflected. In some embodiments, the entire insertion tube can be rigid. In some embodiments, the insertion tube can be made primarily of plastic, metal, silicone, or any combination thereof.

The medical scope can include a fluid reservoir positioned within the elongate controller housing and including a fluid cavity that is constructed and arranged to be in fluid communication with at least a first irrigation channel positioned inside the insertion tube.

The medical scope can include one or more fluid pumps positioned within the elongate controller housing and in fluid communication with the fluid cavity, the one or more fluid pumps being constructed and arranged to pump fluid from the fluid reservoir and into the first irrigation channel. The one or more fluid pumps can pump fluid into the first irrigation channel to pump fluid out of a fluid outlet of the first irrigation channel. Fluid can be pumped out of the fluid outlet to irrigate any cavity or orifice of the human body.

The medical scope can include a camera positioned at a first end portion of the insertion tube. The medical scope can be configured to generate and wirelessly send image data and/or video data to a computing device located at a suitable distance from the medical scope.

Referring to FIG. 1, a medical scope 10 can include a handheld controller 12. In some embodiments, the handheld controller 12 can include an elongate controller housing 14 sized to be operable by one hand (e.g., 40 in FIG. 4) of a user (e.g., 41 in FIG. 4). In some embodiments, an insertion tube 20 can be constructed and arranged to be connected to the elongate controller housing 14. At least a first end portion 24 of the insertion tube 20 can be constructed and arranged to be deflected. In some embodiments, a second end portion 21 can connect the first end portion 24 of the insertion tube 20 to the elongate controller housing 14. In some embodiments, the insertion tube 20 can include an articulated portion 22 between the first end portion 24 and the second end portion 21. In some embodiments, the articulated portion 22 can be proximate to the first end portion 24.

Figures 2, 3:
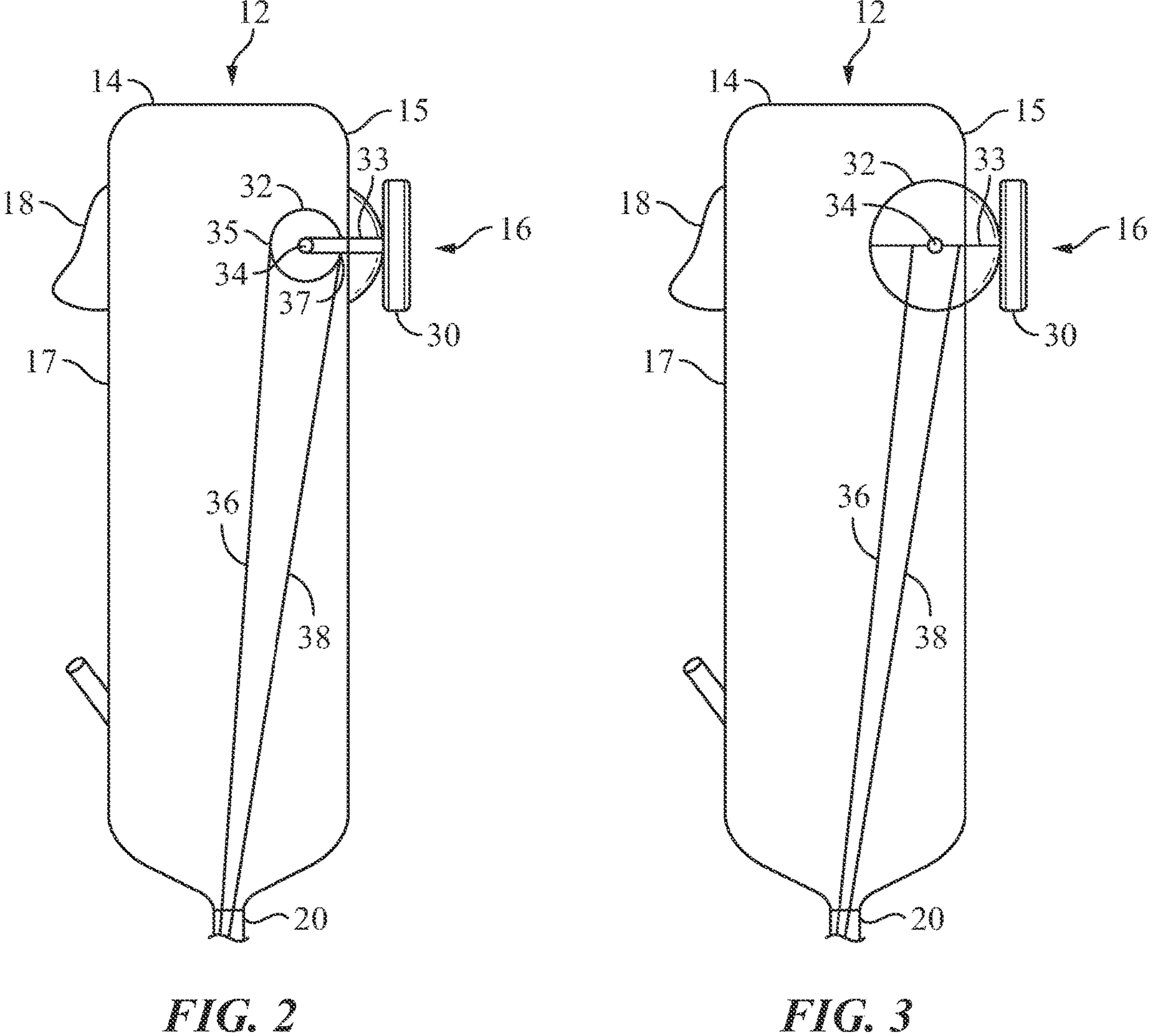
FIG. 2 illustrates a cross-sectional view of a medical scope, according to some embodiments disclosed herein.
FIG. 3 illustrates a cross-sectional view of a medical scope, according to some embodiments disclosed herein.

Referring to FIG. 2, in some embodiments, the handheld controller 12 can include a first control 16 proximate to a first side 15 of the elongate controller housing 14. In some embodiments, one or more cables or wires 36, 38 can be positioned within at least the insertion tube 20 and the elongate controller housing 14. In some embodiments, the one or more cables or wires 36, 38 can be constructed and arranged to connect at least the first control 16 to the first end portion 24 of the insertion tube 20.

In some embodiments, the first control 16 can be a tension control. For example, the first control 16 can be constructed and arranged to tension at least one cable or wire 36 or 38. In some embodiments, the first control 16 can include a joystick 30 connected to a wheel 32. A first cable or wire 36 can be attached to a first portion 35 of the wheel 32. A second cable or wire 38 can be attached to a second portion 37 of the wheel 32. The joystick 30 can be attached and rotationally fixed to the wheel 32. The joystick 30 and the wheel 32 can be rotatably connected to a pivot 34 that is attached to the controller housing 14. As the joystick 30 is rotated, the wheel 32 can rotate with the joystick in either a clockwise or counterclockwise direction. Rotating the joystick 30 in a first direction (e.g., clockwise) about the pivot 34 can cause the first cable or wire 36 to tension (e.g., including to have increased tension) while allowing the second cable or wire 38 to have reduced tension or no tension. Rotating the joystick 30 in a second direction (e.g., counterclockwise) opposite the first direction about the pivot 34 can cause the second cable or wire 38 to tension while allowing the first cable or wire 36 to have reduced tension or no tension. The joystick 30 can include a lever 33 connected to the pivot 34. The lever 33 can be in mechanical communication with the one or more cables or wires 36, 38.

Referring to FIG. 3, the wheel 32 can be integrated with the joystick 30 so as to form a dial (not separately labeled from the wheel 32). The dial 32 can partially protrude out of the controller housing 14.

Figure 4:
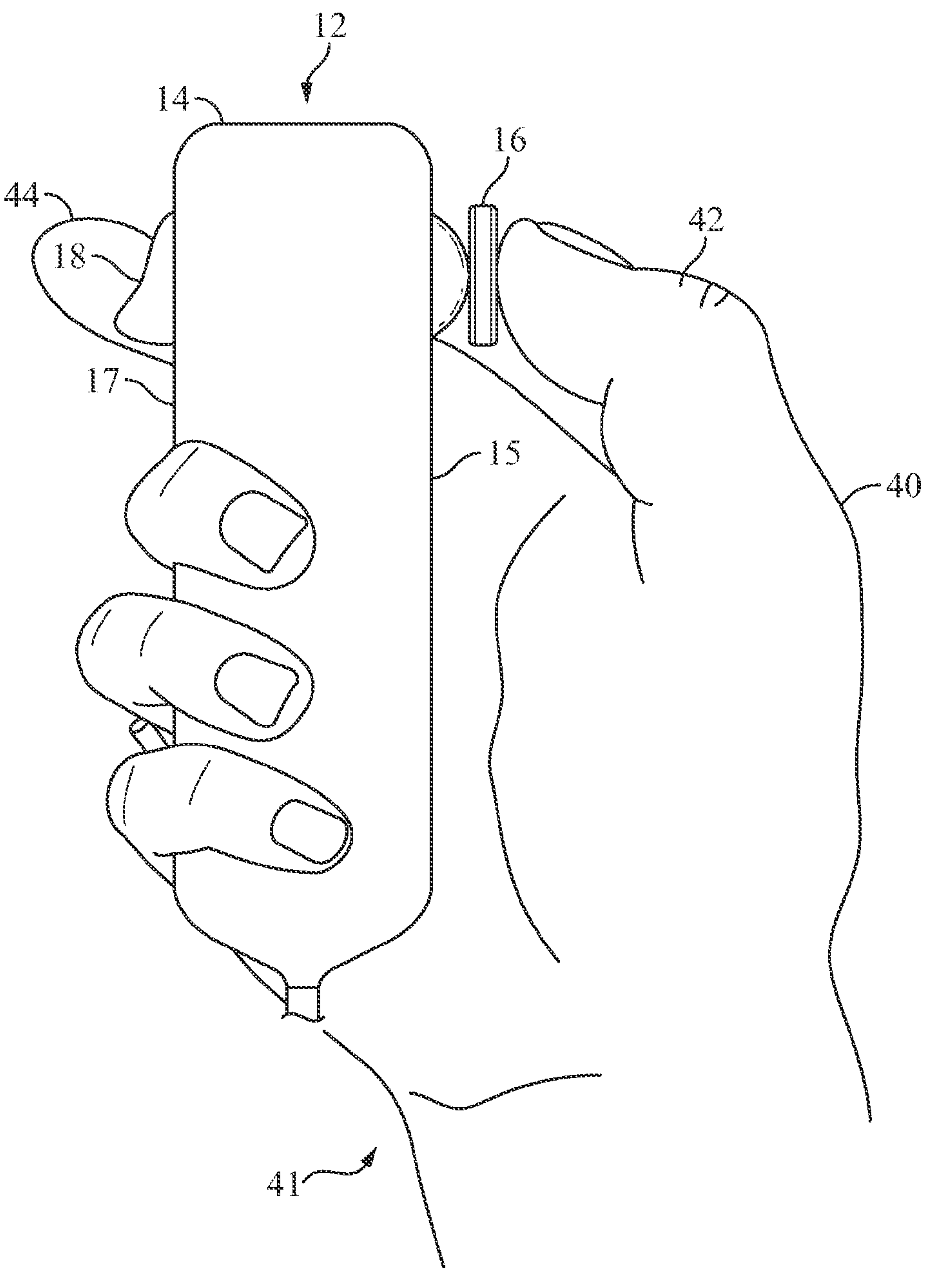
FIG. 4 illustrates an example one hand mode of operation of a medical scope, according to some embodiments disclosed herein.

Referring to FIG. 4, during the one hand mode of operation the first control 16 can be positioned so as to be actuated by one thumb 42 of one hand 40 of the user 41 to tension at least a first cable or wire (e.g., 36 or 38 in FIGS. 2 and 3) of the one or more cables or wires (e.g., 36, 38 in FIGS. 2 and 3) to deflect at least the first end portion (e.g., 24 in FIG. 1) of the insertion tube (e.g., 20 in FIG. 1).

Figure 9:
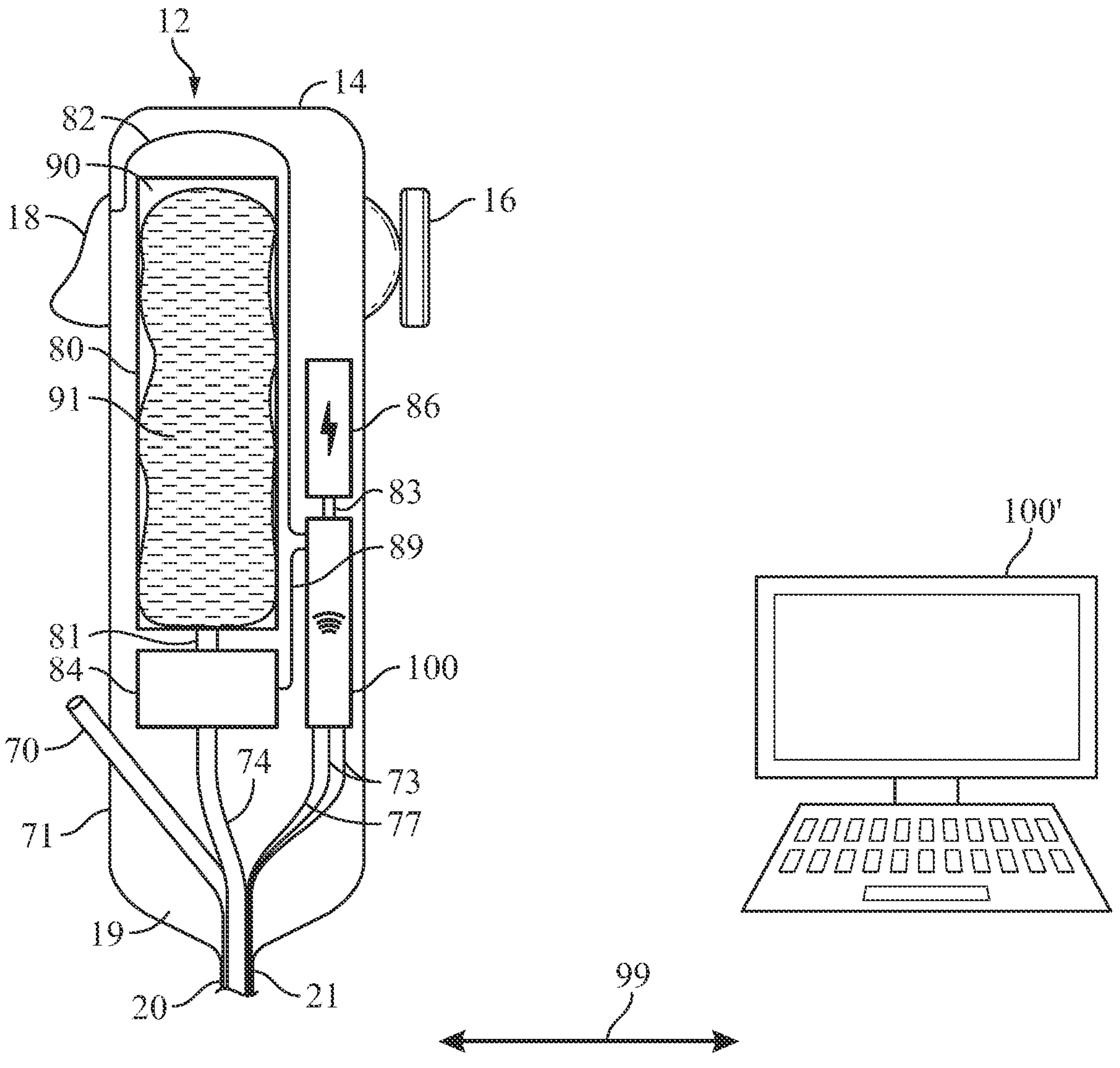
FIG. 9 illustrates a computing device located within a distance from a medical scope, and components inside a controller housing of a medical scope, according to some embodiments disclosed herein.

In some embodiments, the handheld controller 12 can include a second control 18 positioned so as to be actuated by one or more fingers 44 of the one hand 40 of the user 41 to activate one or more pumps (e.g., 84 in FIG. 9). In some embodiments, the second control 18 can be proximate to a second side 17 opposite the first side 15 of the elongate controller housing 14.

Figure 5:
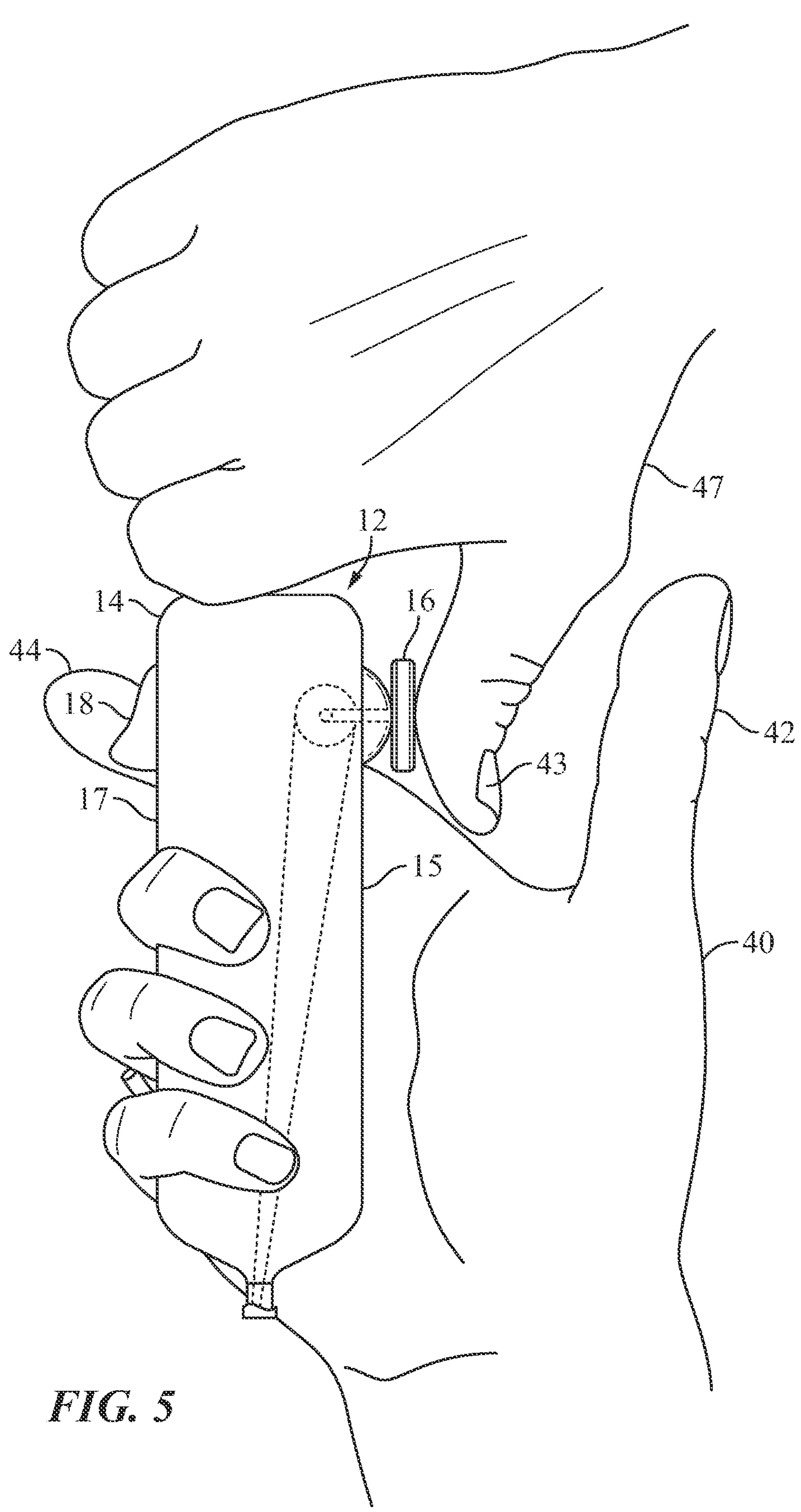
FIG. 5 illustrates an example two hand mode of operation of a medical scope, according to some embodiments disclosed herein.

Referring to FIG. 5, during a two hand mode of operation, the second control 18 can be positioned so as to be actuated by one or more fingers 44 of one hand 40 of the user 41 to activate one or more pumps (e.g., 84 in FIG. 9). The first control 16 can be positioned so as to be actuated by one thumb 43 of another hand 47 of the user 41 to tension at least a first cable or wire (e.g., 36 or 38 in FIGS. 2 and 3) of the one or more cables or wires (e.g., 36, 38 in FIGS. 2 and 3) to deflect at least the first end portion (e.g., 24 in FIG. 1) of the insertion tube (e.g., 20 in FIG. 1).

Figure 6C:
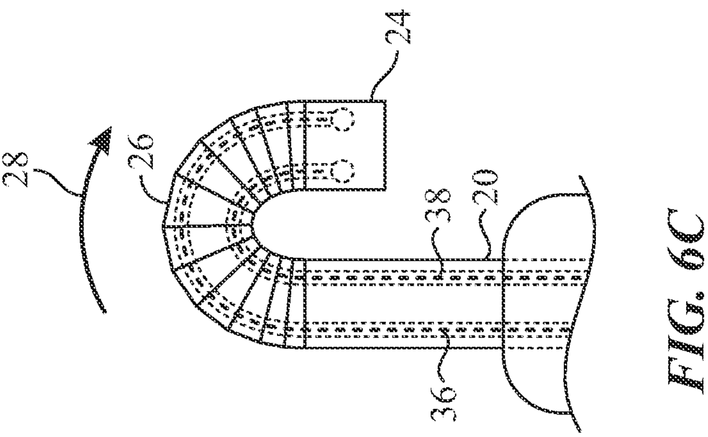
FIGS. 6A to 6C illustrate a deflectable end portion of an insertion tube of a medical scope, according to some embodiments disclosed herein.
Figure 6B:
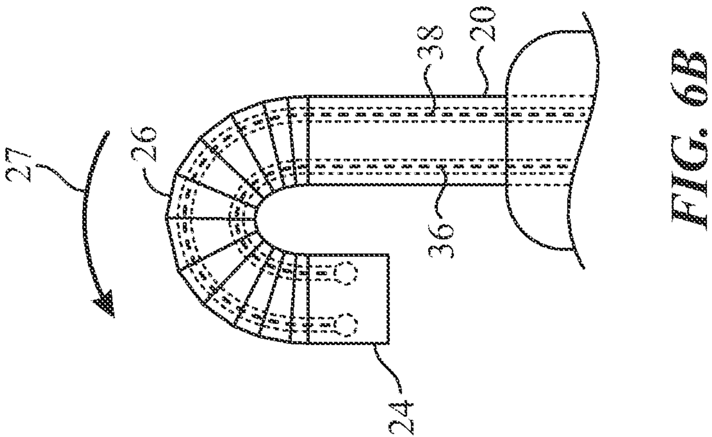
Figure 6A:
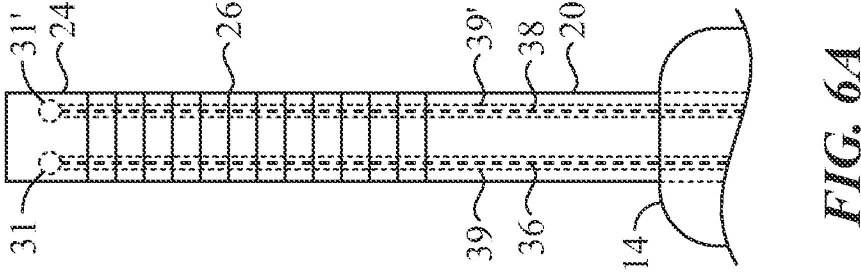

Referring to FIG. 6A, the insertion tube 20 can include an articulated portion 26. A first cable or wire 36 can be positioned within a first channel 39 inside the insertion tube 20. The first cable or wire 36 can be connected to a first stop 31 received in, or otherwise attached to the first end portion 24 of the insertion tube 20. A second cable or wire 38 can be positioned within a second channel 39' inside the insertion tube 20. The second cable or wire 38 can be connected to a second stop 31' received in, or otherwise attached to the first end portion 24 of the insertion tube 20.

Referring to FIG. 6B, when the first cable or wire 36 is tensioned, the end portion 24 can be deflected in generally a first (e.g., counterclockwise) direction 27. Referring to FIG. 6C, when the second cable or wire 38 is tensioned, the end portion 24 can be deflected in generally a second (e.g., clockwise) direction 28 opposite the first direction 27.

Figure 7A:
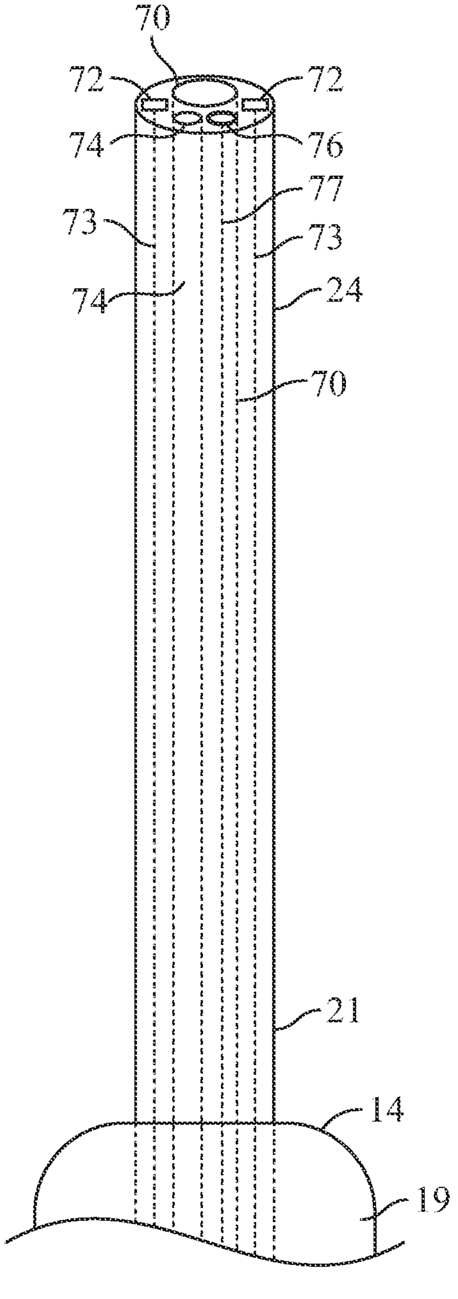
FIG. 7A illustrates a perspective view of an end portion of an insertion tube of a medical scope, according to some embodiments disclosed herein.
Figure 7B:
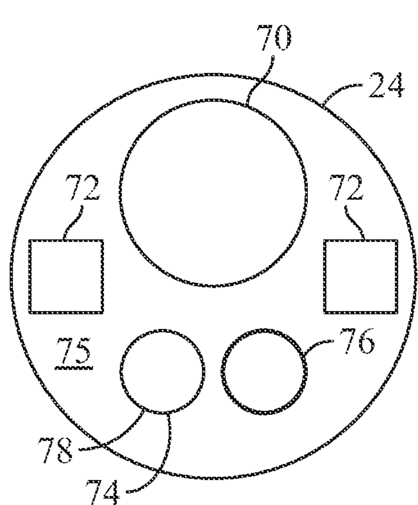
FIG. 7B illustrates a top view of an end portion of an insertion tube of a medical scope, according to some embodiments disclosed herein.

Referring to FIGS. 7A and 7B, one or more cameras 76 can be positioned at the first end portion 24 of the insertion tube 20. The one or more cameras 76 can be electrically connected to one or more electrical connections 77 that extend at least from inside 19 the housing 14 to the first end portion 24 of the insertion tube 20.

In some embodiments, one or more light sources 72 can be positioned at the first end portion 24 of the insertion tube 20. In some embodiments, the one or more light sources 72 can include any suitable light sources such as, for example, light emitting diodes. In some embodiments, the one or more light sources 72 can be electrically connected to one or more electrical connections 73 that extend at least from inside 19 the housing 14 to the first end portion 24 of the insertion tube 20.

In some embodiments, one or more working channels 70 can be positioned within the insertion tube 20. In some embodiments, the one or more working channels 70 can extend at least from inside 19 the housing 14 to the first end portion 24 of the insertion tube 20. In some embodiments, the one or more working channels 70 can extend to an exterior surface 75 of the first end portion 24. The proximate end of the working channel can accommodate a connection to additional external appliances, even allowing for additional irrigation fluid to be passed via the working channel if needed.

In some embodiments, one or more irrigation channels 74 can be positioned within the insertion tube 20. The one or more irrigation channels 74 can be constructed and arranged to extend at least from inside 19 the housing 14 to the first end portion 24 of the insertion tube 20. In some embodiments, the one or more irrigation channels 74 can extend to the exterior surface 75 of the first end portion 24, forming an outlet 78 defined by the exterior surface 75.

Figure 8A:
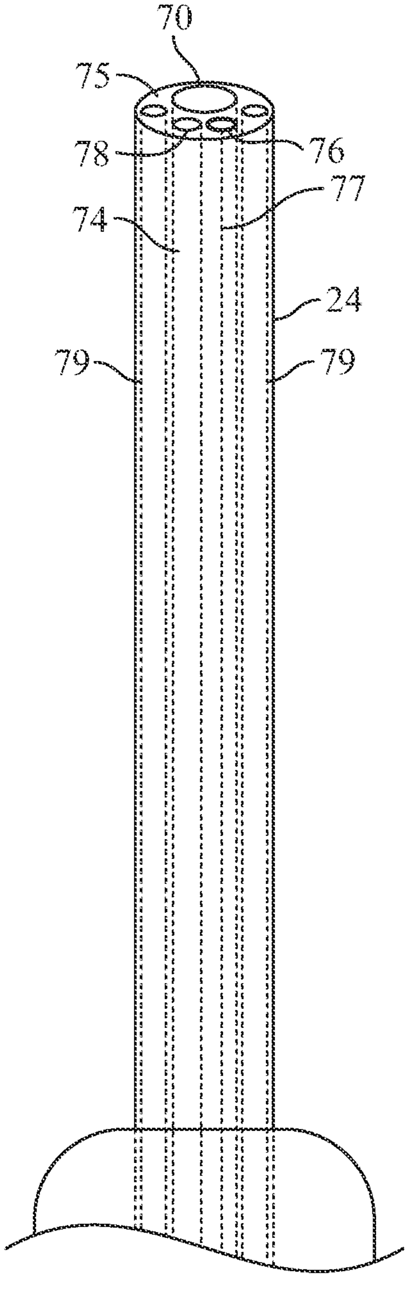
FIG. 8A illustrates a perspective view of an end portion of an insertion tube of a medical scope, according to some embodiments disclosed herein.
Figure 8B:
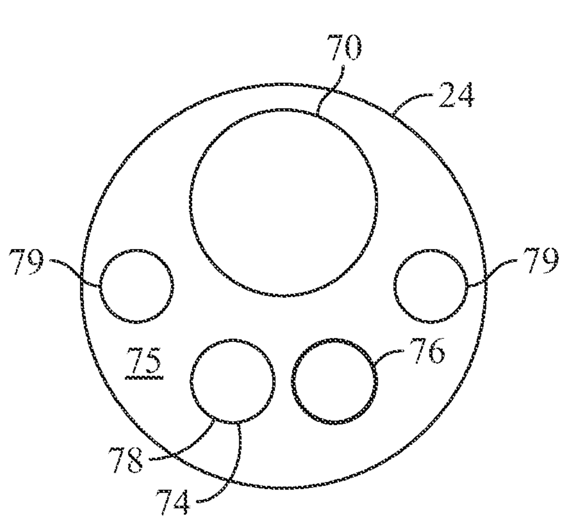
FIG. 8B illustrates a top view of an end portion of an insertion tube of a medical scope, according to some embodiments disclosed herein.

Referring to FIGS. 8A and 8B, one or more optical connections 79 can extend at least from inside 19 the housing 14 to the exterior surface 75 first end portion 24 of the insertion tube 20. In some embodiments, the one or more optical connections 79 can include any suitable connections for transmitting light such as, for example, fiber optic connections.

Referring to FIG. 9, one or more working channels 70 can be constructed and arranged to extend at least from an exterior surface 71 of the elongate controller housing 14 to the first end portion (e.g., 24 in FIGS. 7A and 7B) of the insertion tube 20. In some embodiments, the one or more working channels 70 can be constructed and arranged to extend at least from an exterior surface 71 of the elongate controller housing 14 to the inside 19 of the housing 14, and extend from the inside 19 of the housing 14 to the second end portion 21 of the insertion tube 20.

A fluid reservoir 80 can be positioned within the elongate controller housing 14 and include a fluid cavity 90 that is constructed and arranged to be in fluid communication with at least one or more irrigation channels 74 positioned inside the insertion tube 20 and the housing 14. In some embodiments the fluid reservoir 80 can be constructed and arranged to contain any suitable fluid such as, for example, a gas 91. In some embodiments, the gas 91 can include carbon dioxide.

One or more fluid pumps 84 positioned within the elongate controller housing 14 can be in operative communication with the second control 18. The one or more fluid pumps 84 can be constructed and arranged to be in fluid communication with the fluid cavity 90. In some embodiments, a fluid connection 81 can connect the fluid reservoir 80 to the one or more pumps 84.

In some embodiments, a computing device 100 positioned within the elongate controller housing 14 can be in electrical communication with the second control 18 and the one or more fluid pumps 84. The second control 18 can be electrically connected to the computing device 100 by an electrical connection 82. The computing device 100 can be electrically connected to the one or more pumps 84 by another electrical connection 89. In some embodiments, in response to detecting that the second control 18 is actuated, the computing device 100 can activate the one or more fluid pumps 84. In some embodiments, the second control 18 can be an electrical switch such as, for example, a push button.

The one or more fluid pumps 84 can be constructed and arranged to pump fluid such as the gas 91 from the fluid reservoir 80 and into the one or more irrigation channels 74 when activated. After being pumped into the one or more irrigation channels 74, the fluid 91 can be pumped out of an outlet (e.g., 78 in FIG. 7B) of the one or more irrigation channels 74.

One or more batteries 86 can be positioned inside the elongate controller housing 14. The one or more batteries 86 can be constructed and arranged to provide power to at least the one or more fluid pumps 84, the one or more cameras (e.g., 76 in FIGS. 7A, 7B, 8A, 8B), the one or more light sources (e.g., 72 in FIGS. 7A and 7B), one or more processors (e.g., 202 in FIG. 16), or any combination thereof. The one or more batteries 86 can be electrically connected to the computing device 100 by an electrical connection 83.

In some embodiments, one or more light sources (e.g., 72 in FIGS. 7A and 7B) can be electrically connected to the computing device 100 by the one or more electrical connections 73. In some embodiments, the computing device 100 can be configured to at least activate the one or more light sources. The one or more light sources can generate light when activated.

In some embodiments, the one or more cameras (e.g., 76 in FIGS. 7A, 7B, 8A, 8B) can be electrically connected to the computing device 100 by the one or more electrical connections 77. In some embodiments, the computing device 100 can be configured to at least activate the one or more cameras. The one or more cameras can record images and/or video(s) and send image and/or video data to the computing device 100 when activated.

In some embodiments, the computing device 100 can be configured to receive image data and/or video data from the one or more cameras; and wirelessly send, through one or more antennas (e.g., 216 in FIG. 16), the image data and/or video data to another computing device 100' located at a distance 99 from the one or more antennas in the computing device 100. The distance 99 can be a predetermined distance to prevent other devices located at farther distances from receiving the image and/or video data.

Figure 10:
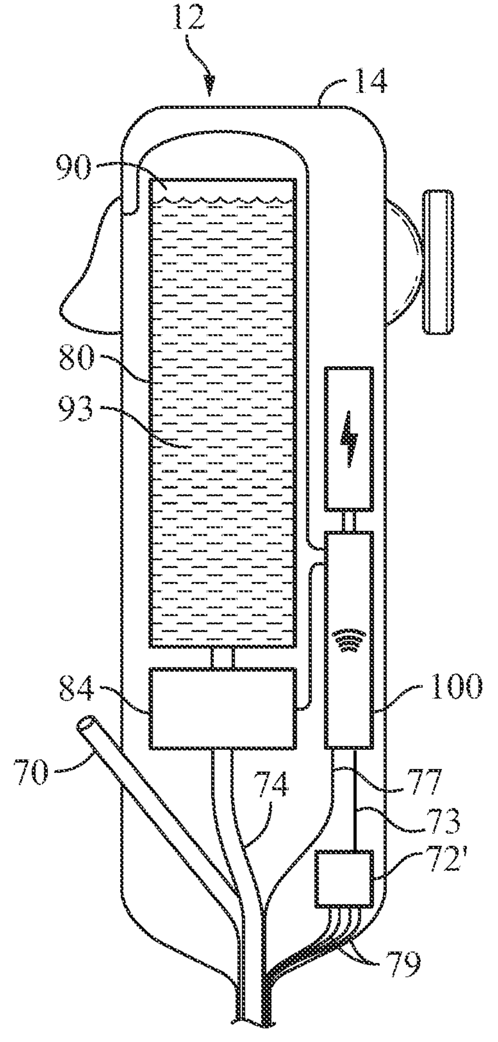
FIG. 10 illustrates components inside a controller housing of a medical scope, according to some embodiments disclosed herein.

Referring to FIG. 10, one or more optical connections 79 can be connected to one or more light sources 72' positioned within the elongate controller housing 14. The one or more optical connections 79 can be constructed and arranged to guide light generated by the one or more light sources 72' to at least an exterior surface (e.g., 75 in FIG. 8B) of the first end portion (e.g., 24 in FIG. 8B).

In some embodiments, the fluid reservoir 80 can be constructed and arranged to contain any suitable fluid such as, for example, a liquid 93. In some embodiments, the liquid 93 can include water. The one or more fluid pumps 84 can be constructed and arranged to pump fluid such as liquid 93 from the fluid reservoir 80 and into the one or more irrigation channels 74 when activated. After being pumped into the one or more irrigation channels 74, the fluid 93 can be pumped out of an outlet (e.g., 78 in FIG. 7B) of the one or more irrigation channels 74.

Figure 11:
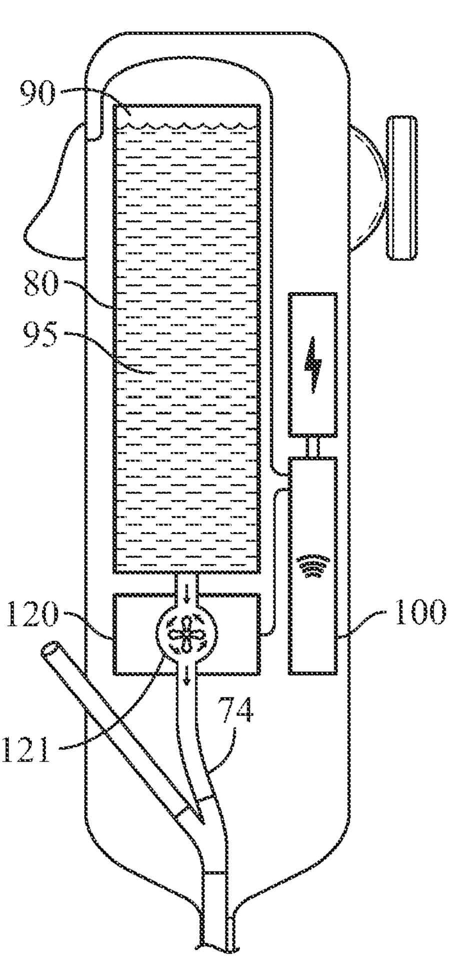
FIG. 11 illustrates components inside a controller housing of a medical scope, according to some embodiments disclosed herein.

Referring to FIG. 11, the one or more fluid pumps 84 can include a fan pump 120 electrically connected to the computing device 100. In some embodiments, the fan pump can include a fan 121 in fluid communication with the fluid cavity 90 of the fluid reservoir 80. When the fan pump 120 is activated, the fan 121 is rotated to pump fluid 95 from the fluid reservoir 80 and into the one or more irrigation channels 74.

Figure 12:
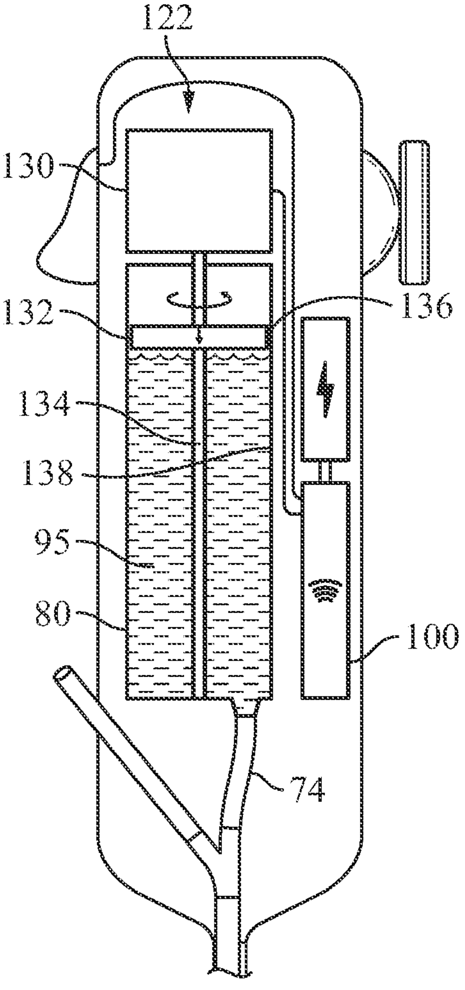
FIG. 12 illustrates components inside a controller housing of a medical scope, according to some embodiments disclosed herein.

Referring to FIG. 12, the one or more fluid pumps 84 can include a threaded rod pump 122. In some embodiments, the threaded rod pump 122 can include a motor 130 electrically connected to the computing device 100. The motor 130 can be in rotational communication with a threaded rod 134. The threaded rod 134 can be in threaded communication with a threaded piston 132. An inner surface 138 of the fluid reservoir 80 can be engaged with an outer surface 136 of the threaded piston 132 to prevent the threaded piston 132 from rotating relative to the fluid reservoir 80. When the threaded rod pump 122 is activated, the motor 130 rotates the threaded rod 134. As the threaded piston 132 is prevented from rotating with the threaded rod 134, the threaded piston 132 can move along the threaded rod 134. Changing a direction in which the threaded rod 134 rotates can change a direction in which the threaded piston 132 moves along the threaded rod 134.

In some embodiments, the threaded piston 132 can form a fluid seal with the fluid reservoir 80 so that as the threaded piston 132 moves along the threaded rod 134 and toward the one or more irrigation channels 74, the threaded piston 132 can pump fluid 95 from the fluid reservoir 80 and into the one or more irrigation channels 74.

Figure 13A:
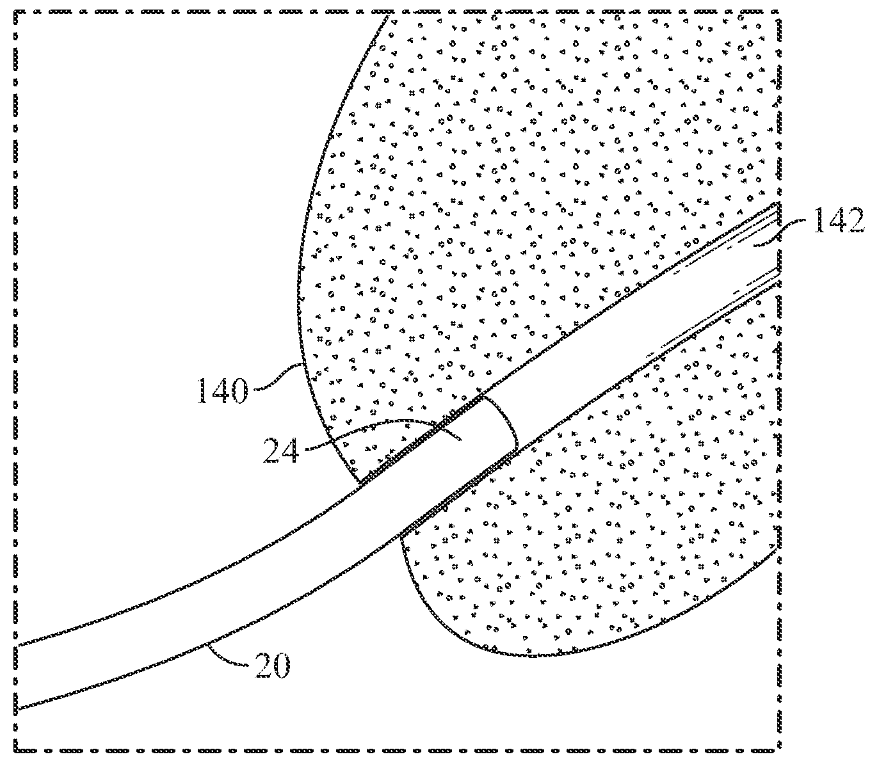
FIG. 13A illustrates an insertion tube inserted in a cavity or orifice of a patient, according to some embodiments disclosed herein.

Referring to FIG. 13A, the insertion tube 20 can be constructed and arranged to be inserted into any suitable cavity or orifice 142 of a patient 140 (e.g., a human body or an animal body). For example, the cavity or orifice 142 can include a vaginal cavity, a colon, an airway, a lung cavity, a uterine cavity, etc.

Figure 13B:
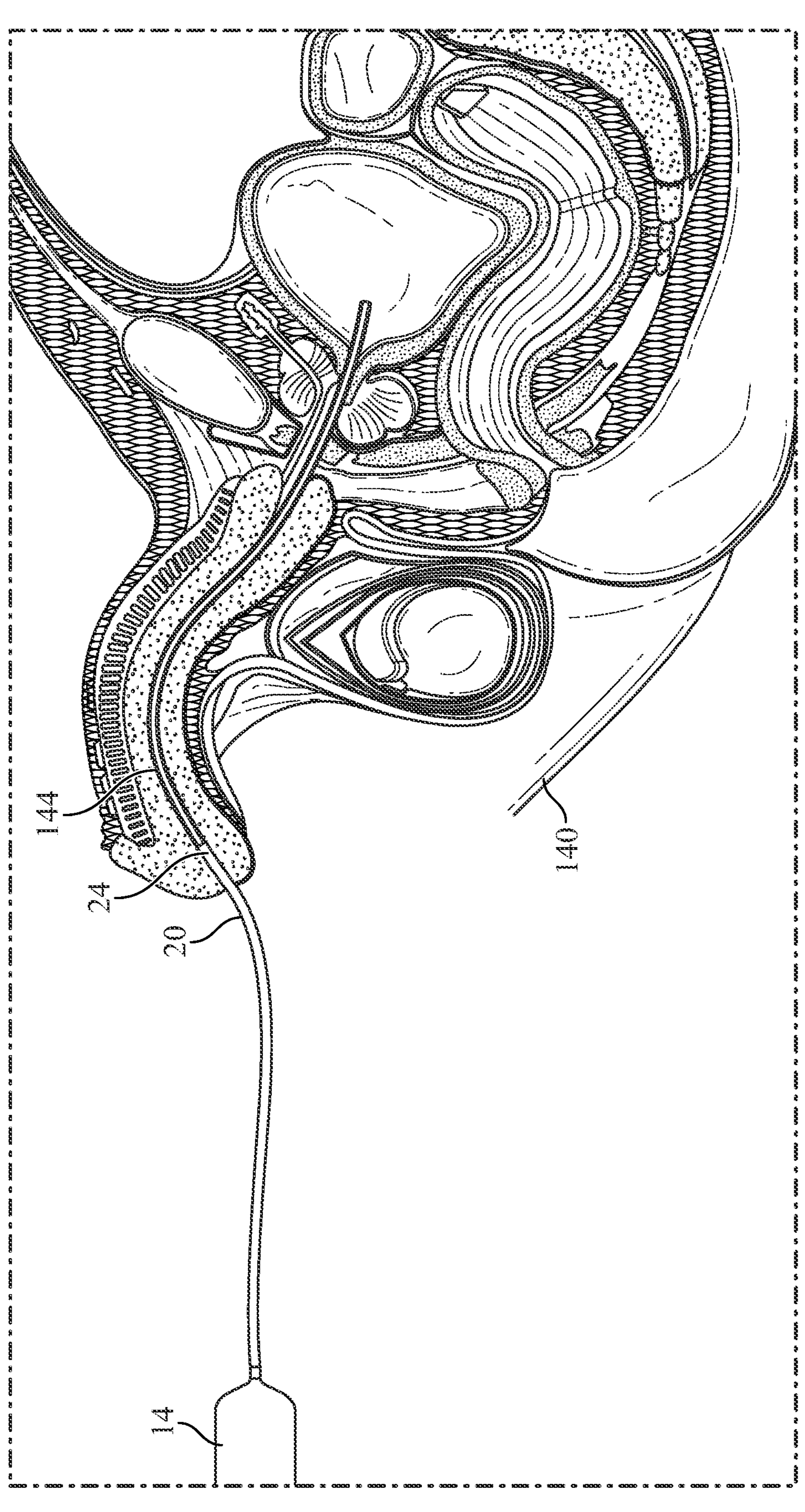
FIG. 13B illustrates an insertion tube inserted in a urethra of a patient, according to some embodiments disclosed herein.
Figure 13C:
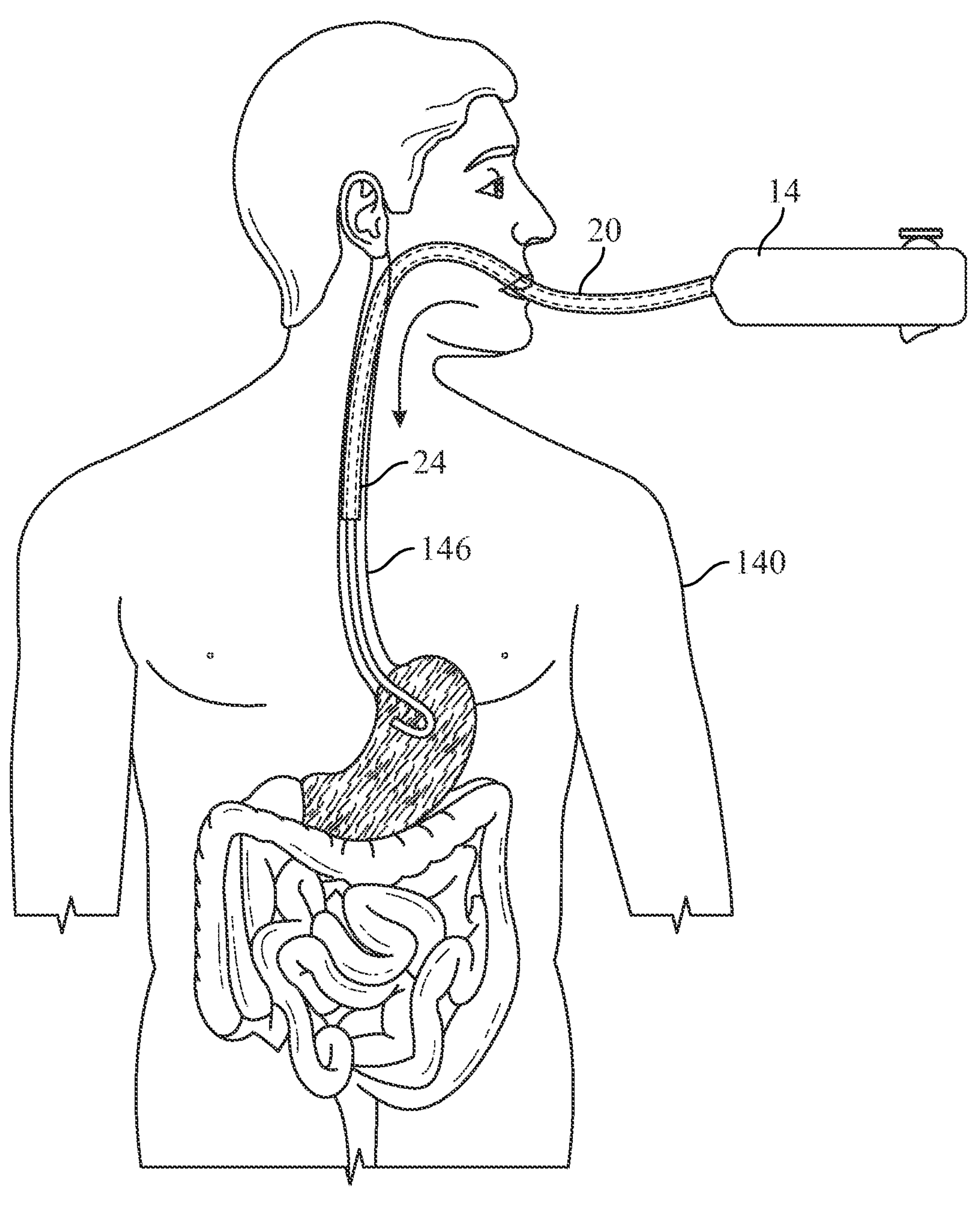
FIG. 13C illustrates an insertion tube inserted in an esophagus of a patient, according to some embodiments disclosed herein.

As another example, referring to FIG. 13B, the insertion tube 20 can be constructed and arranged to be inserted into a urethra 144 of a patient 140. Referring to FIG. 13C, the insertion tube 20 can be constructed and arranged to be inserted into an esophagus 146 of a patient 140.

Figure 14A:
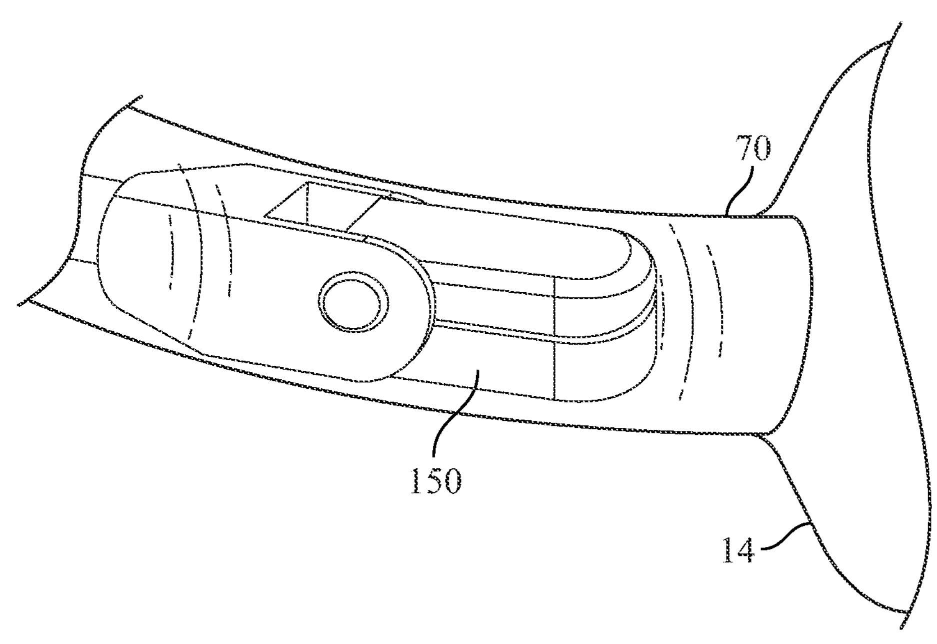
FIG. 14A illustrates biopsy forceps received in a working channel, according to some embodiments disclosed herein.
Figure 14B:
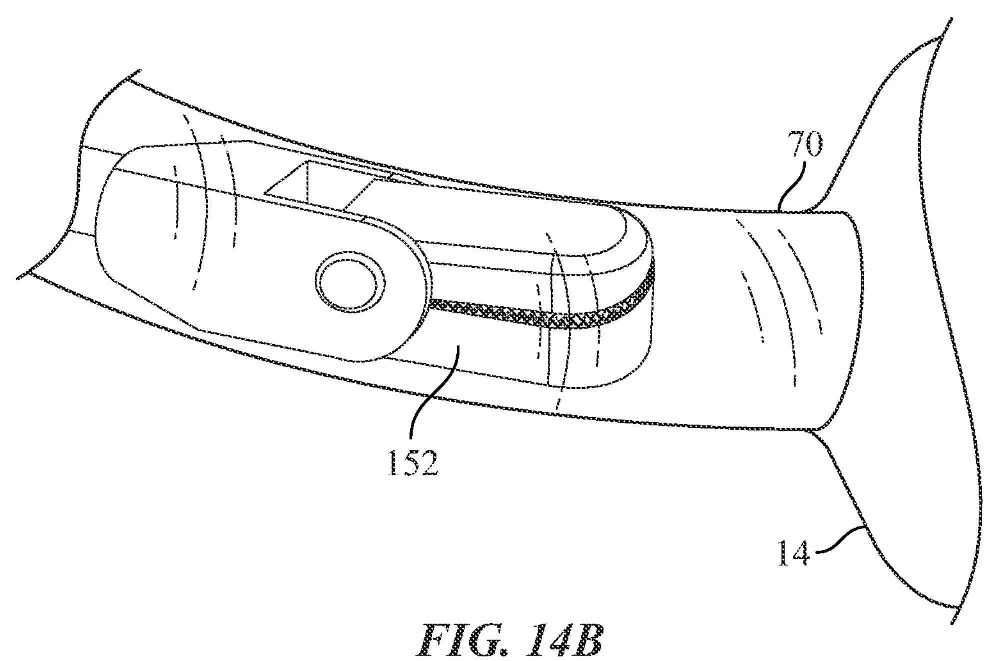
FIG. 14B illustrates grasping forceps received in a working channel, according to some embodiments disclosed herein.
Figures 14C, 14D:
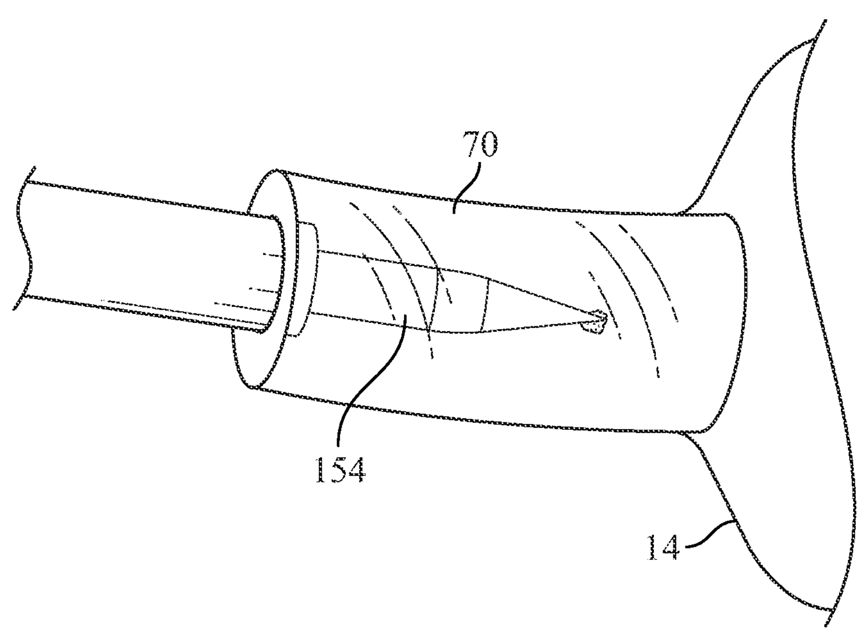
FIG. 14C illustrates a fulguration electrode received in a working channel, according to some embodiments disclosed herein.
FIG. 14D illustrates a guide wire received in a working channel, according to some embodiments disclosed herein.

Referring to FIG. 14A, the working channel 70 can be constructed and arranged to receive biopsy forceps 150. Referring to FIG. 14B, the working channel 70 can be constructed and arranged to receive grasping forceps 152. Referring to FIG. 14C, the working channel 70 can be constructed and arranged to receive a fulguration electrode 154. Referring to FIG. 14D, the working channel 70 can be constructed and arranged to receive a guide wire 156.

Figure 15:
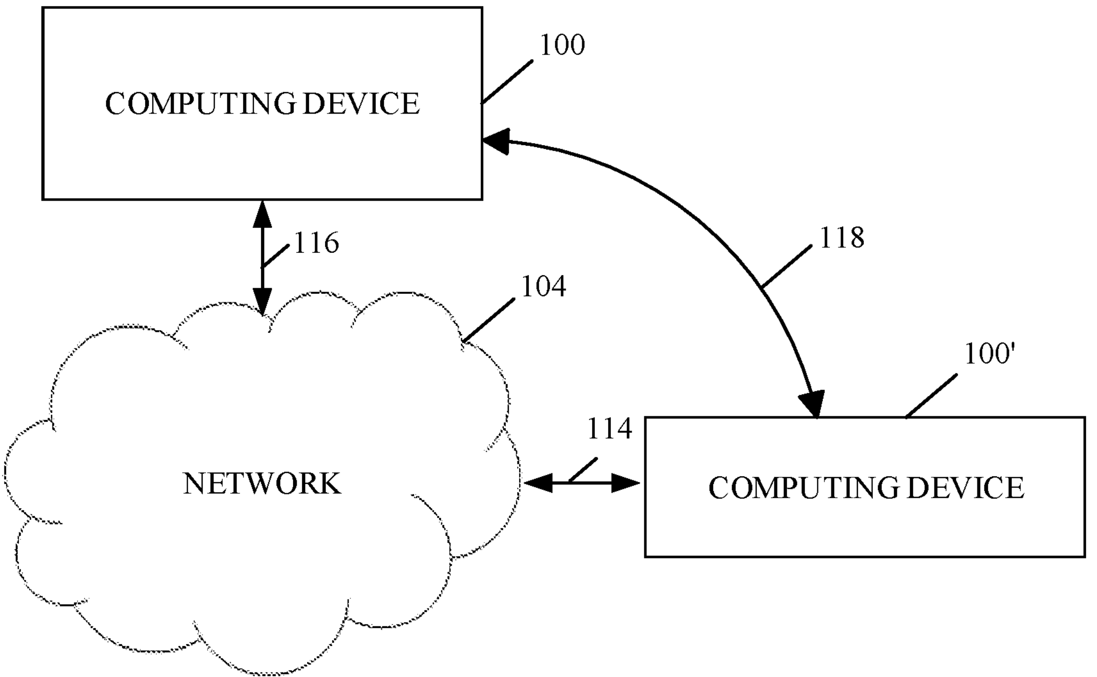
FIG. 15 illustrates a block diagram of a system for wirelessly connecting the medical scope to a computing device, according to some embodiments disclosed herein.

Referring to FIG. 15, a system for connecting the computing device 100 in a medical scope to a second computing device 100' is shown. In some embodiments, the system can comprise the computing device 100, a network 104 (e.g., a communication network), a second computing device 100', or any combination thereof.

The computing device 100 can be any suitable computing device(s) for storing data, programs, or a combination thereof, for receiving image data and/or video data from the one or more cameras (e.g., 76 in FIGS. 7A and 7B), and for wirelessly sending, through one or more antennas (e.g., 216 in FIG. 16), the image data and/or video data to the second computing device 100'. In some embodiments, the image data can include video frame data. In some embodiments, the image data can include images. In some embodiments, the video data can include video frames.

The second computing device 100' can be any suitable computing device(s) for storing data, programs, or a combination thereof, for wirelessly receiving image data and/or video data from the computing device 100.

The network 104 can include a wired network, a wireless network, or a combination thereof. In some embodiments, the network 104 can include the Internet, an intranet, a wide-area network (WAN), a local-area network (LAN), a digital subscriber line (DSL) network, a frame relay network, an asynchronous transfer mode (ATM) network, a virtual private network (VPN), any other suitable communication network, or any combination thereof. In some embodiments, one or more communications links 114 can connect the second computing device 100' to the network 104. In some embodiments, one or more communication links 116 can connect the network 104 to the computing device 100. In some embodiments, one or more communication links 118 can wirelessly connect the computing device 100 to the second computing device 100'. In some embodiments, the one or more communication links 114, 116, 118 can be any communication links suitable for communicating information between the computing device 100 and the second computing device 100', such as, for example, network links, dial-up links, wireless links, hard-wired links, any other suitable communications links, or any combination thereof.

The computing device 100 and/or the second computing device 100' can include a mobile device, such as a mobile phone, a tablet computer, a wearable computer, a laptop computer, a vehicle (e.g., a car, a boat, an airplane, or any other suitable vehicle), any other suitable mobile device, any suitable non-mobile device (e.g., a desktop computer, entertainment system, etc.), or any combination thereof. As another example, the computing device 100 and/or the second computing device 100' can include a media playback device, such as a television, a projector device, a game console, any other suitable computing device, or any combination thereof.

Although one second computing device is shown in FIG. 15 to avoid over-complicating the figure, the computing device 100 can communicate with any suitable number of second computing devices 100' in some embodiments.

In some embodiments, the computing device 100 and/or the second computing device 100' can be implemented using any suitable hardware. For example, the computing device 100 and/or the second computing device 100' can be implemented using any suitable general-purpose computer or special-purpose computer. Any general-purpose computer or special-purpose computer can include any suitable hardware.

Figure 16:
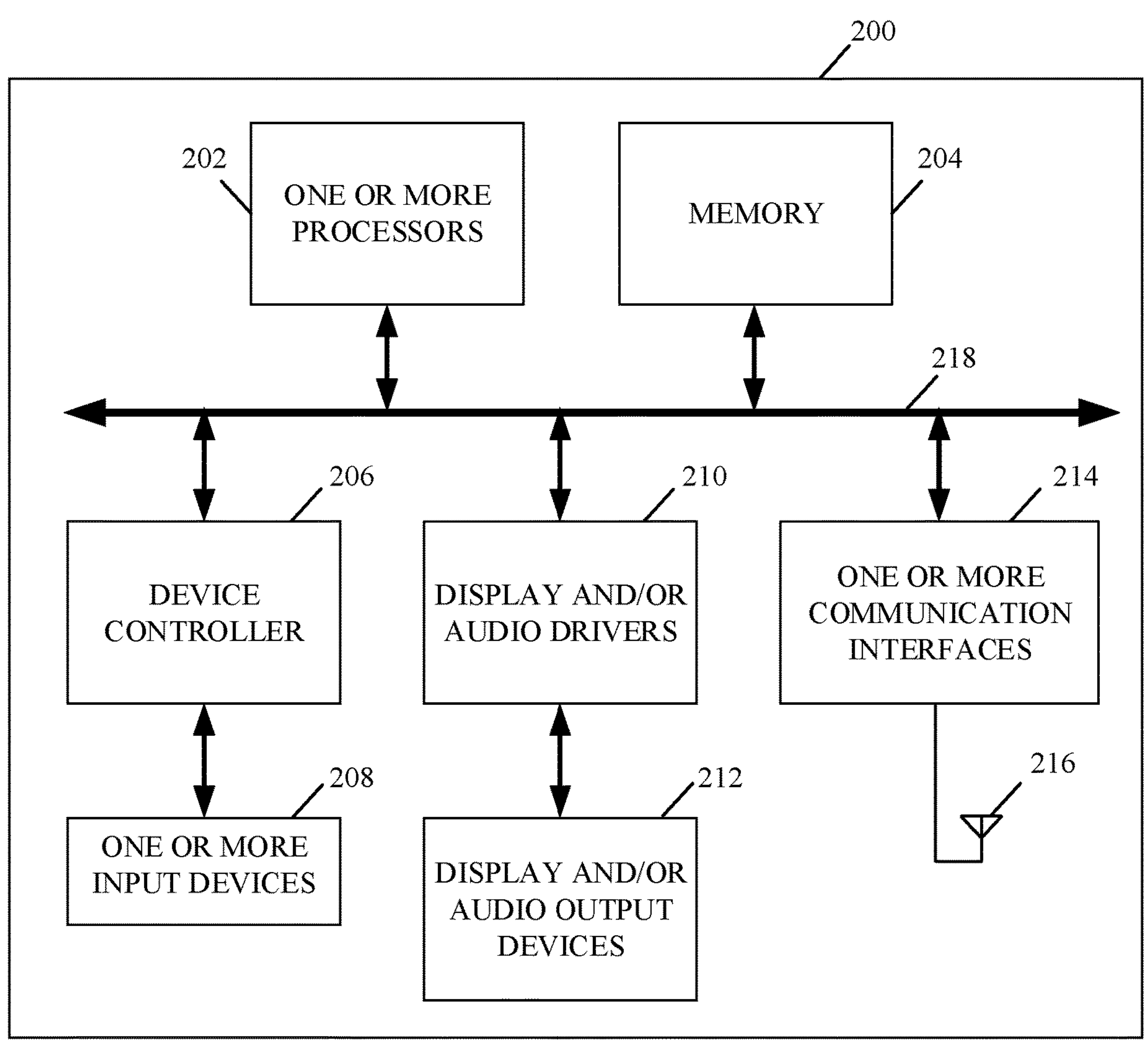
FIG. 16 illustrates a block diagram of a computing device, according to some embodiments disclosed herein.

Referring to FIG. 16, an example hardware of a computing device 200 is illustrated. In some embodiments, the computing device 200 can include one or more processors 202, memory 204, and one or more antennas 216. In some embodiments, the computing device 200 can further include a device controller 206, one or more input devices 208, display and/or audio drivers 210, display and/or audio output devices 212, one or more communication interfaces 214, a bus 218, or any combination thereof.

In some embodiments, the one or more processors 202 can include any suitable hardware processor, such as a central processing unit (CPU), a graphics processing unit (GPU), a tensor processing unit (TPU), an accelerated processing unit (APU), any other type of processing unit, or any combination thereof. In some embodiments, the one or more processors 202 can include a microprocessor, a controller, a micro-controller, a digital signal processor, dedicated logic, an application-specific integrated circuit (ASIC), a field programmable gate array (FPGA), an accelerator (e.g., an artificial intelligence (AI) accelerator or a cryptographic accelerator), any other suitable circuitry for controlling the functioning of a general purpose computer or a special purpose computer, or any combination thereof.

In some embodiments, one or more processors 202 can be in operative communication with at least the memory 204, one or more cameras (e.g., 76 in FIGS. 7A and 7B), and the one or more antennas 216. The one or more processors 202 can be configured at least to: receive image data and/or video data from the one or more cameras; and wirelessly send, through the one or more antennas 216, the image data and/or video data to another computing device (e.g., 100' in FIG. 15).

In some embodiments, the memory 204 can include any suitable memory, storage, or a combination thereof for storing programs, data, and/or any other suitable information. For example, memory 204 can include volatile memory, non-volatile memory, or any combination thereof. In some embodiments, memory 204 can include random access memory, read-only memory, flash memory, a hard disk drive, a solid state drive, optical media, any other suitable memory, or any combination thereof.

In some embodiments, the device controller 206 can include any suitable processor or circuitry for controlling and receiving any input from the one or more input devices 208. In some embodiments, the one or more input devices 208 can include a touchscreen, a keyboard, a mouse, one or more buttons, a voice recognition circuit, one or more cameras (e.g., 76 in FIGS. 7A and 7B), any other suitable input device, or any combination thereof. In some embodiments, the one or more sensors 220 can include one or more microphones, any other suitable sensors (e.g., an optical sensor, a temperature sensor, a near field sensor), or any combination thereof.

In some embodiments, the display and/or audio drivers 210 can include any suitable circuitry for controlling and driving output to one or more display and/or audio output devices 212. For example, the output devices can include a display (e.g., including a touchscreen, a flat-panel display, a cathode ray tube display, a projector, any other suitable display or presentation device, or any combination thereof), one or more speakers, or a combination thereof.

In some embodiments, the one or more communication interfaces 214 can include any suitable circuitry for interfacing with one or more communication networks (e.g., network 104 in FIG. 15) and/or another computing device (e.g., second computing device 100' in FIG. 15). For example, the one or more communication interfaces 214 can include network interface card circuitry, wired communication circuitry, wireless communication circuitry, any other suitable communication network circuitry, or any combination thereof. In some embodiments, the one or more communication interfaces 214 can include an antenna driver configured to drive the one or more antennas 216. In some embodiments, the one or more communication interfaces 214 can include a WI-FI® communication interface, a BLUETOOTH® communication interface, any other suitable communication interface, or any combination thereof.

In some embodiments, the one or more antennas 216 can wirelessly communicate with a communication network (e.g., network 104) and/or another computing device (e.g., 100' in FIG. 15). In some embodiments, the one or more antennas 216 can include a transmitting antenna, a receiving antenna, a transmitting and receiving antenna, or any combination thereof. In some embodiments, the one or more antennas 216 can include a WI-FI® antenna, a BLUETOOTH® antenna, any other suitable antenna, or any combination thereof. In some embodiments, the one or more antennas 216 can be omitted.

In some embodiments, the bus 218 can include any suitable communication system for communicating data, addresses, control signals, power, or any combination thereof, between two or more components 202, 204, 206, 210, and 214. In some embodiments, the bus 218 can include any suitable conductors that are constructed and arranged to communicate data, addresses, control signals, power, or any combination thereof, between two or more components 202, 204, 206, 210, and 214.

In some embodiments, any other suitable component(s) can be included in the computing device 200.

The following description of variants is only illustrative of components, elements, acts, products, and methods considered to be within the scope of the invention and are not in any way intended to limit such scope by what is specifically disclosed or not expressly set forth. The components, elements, acts, products, and methods as described herein may be combined and rearranged other than as expressly described herein and are still considered to be within the scope of the invention.

According to variation 1, a medical scope can include a handheld controller constructed and arranged to be operated in a one hand mode of operation and in a two hand mode of operation, the handheld controller including: an elongate controller housing sized to be operable by one hand of a user; a first control proximate to a first side of the elongate controller housing; a second control proximate to a second side opposite the first side of the elongate controller housing; an insertion tube constructed and arranged to be connected to the elongate controller housing, wherein at least a first end portion of the insertion tube is constructed and arranged to be deflected; one or more cables or wires positioned within the insertion tube, the one or more cables or wires being constructed and arranged to connect at least the first control to the first end portion of the insertion tube, wherein during the one hand mode of operation the first control is positioned so as to be actuated by one thumb of the user to tension at least a first cable or wire of the one or more cables or wires to deflect at least the first end portion of the insertion tube; one or more irrigation channels positioned within the insertion tube, the one or more irrigation channels being constructed and arranged to extend at least from inside the housing to the first end portion of the insertion tube; a fluid reservoir positioned within the elongate controller housing and including a fluid cavity that is constructed and arranged to be in fluid communication with at least a first irrigation channel of the one or more irrigation channels positioned inside the insertion tube; one or more fluid pumps in operative communication with the second control and constructed and arranged to be in fluid communication with the fluid cavity, the one or more fluid pumps being constructed and arranged to pump fluid from the fluid reservoir and into the one or more irrigation channels, wherein during the one hand mode of operation the second control is positioned so as to be actuated by one or more fingers of the user to activate the one or more fluid pumps; one or more cameras positioned at the first end portion of the insertion tube; memory positioned within the elongate controller housing; one or more antennas positioned within the elongate controller housing; one or more processors positioned within the elongate controller housing, wherein the one or more processors are in operative communication with at least the memory, the one or more cameras, and the one or more antennas, wherein the one or more processors are configured at least to: receive image data from the one or more cameras; and wirelessly send, through the one or more antennas, the image data to a computing device located within a predetermined distance from the one or more antennas.

Variation 2 can include the medical scope of variation 1, further comprising: one or more working channels positioned within the insertion tube, the one or more working channels being constructed and arranged to extend at least from an exterior surface of the elongate controller housing to the first end portion of the insertion tube; wherein at least a first working channel of the one or more working channels is constructed and arranged to receive at least biopsy forceps, grasping forceps, a fulguration electrode, a guide wire, or any combination thereof.

Variation 3 can include the medical scope of variation 1, further comprising: one or more batteries constructed and arranged to provide power to at least the one or more fluid pumps, the one or more cameras, and the one or more processors.

Variation 4 can include the medical scope of variation 3, further comprising: one or more light sources positioned at the first end portion of the insertion tube; wherein the one or more batteries are further constructed and arranged to provide power to at least the one or more light sources.

Variation 5 can include the medical scope of variation 1, wherein the first control includes: a lever in mechanical communication with the one or more cables or wires.

Variation 6 can include the medical scope of variation 1, wherein the insertion tube is constructed and arranged to be inserted into a urethra of a patient.

Variation 7 can include the medical scope of variation 1, wherein the insertion tube is constructed and arranged to be inserted into an esophagus of a patient.

Variation 8 can include the medical scope of variation 1, wherein the medical scope is a cystoscope, bronchoscope, a hysteroscope, a vaginoscope, or a colonoscope.

According to variation 9, a medical scope can include a handheld controller constructed and arranged to be operated in a one hand mode of operation and in a two hand mode of operation, the handheld controller including: an elongate controller housing sized to be operable by one hand of a user; a first control proximate to a first side of the elongate controller housing; a second control proximate to a second side opposite the first side of the elongate controller housing; an insertion tube constructed and arranged to be connected to the elongate controller housing, wherein at least a first end portion of the insertion tube is constructed and arranged to be deflected; one or more cables or wires positioned within the insertion tube, the one or more cables or wires being constructed and arranged to connect at least the first control to the first end portion of the insertion tube, wherein during the one hand mode of operation the first control is positioned so as to be actuated by one thumb of the user to tension at least a first cable or wire of the one or more cables or wires to deflect at least the first end portion of the insertion tube; one or more irrigation channels positioned within the insertion tube, the one or more irrigation channels being constructed and arranged to extend at least from inside the housing to the first end portion of the insertion tube; a fluid reservoir positioned within the elongate controller housing and including a fluid cavity that is constructed and arranged to be in fluid communication with at least a first irrigation channel of the one or more irrigation channels positioned inside the insertion tube; one or more fluid pumps in operative communication with the second control and constructed and arranged to be in fluid communication with the fluid cavity, the one or more fluid pumps being constructed and arranged to pump fluid from the fluid reservoir and into the one or more irrigation channels, wherein during the one hand mode of operation the second control is positioned so as to be actuated by one or more fingers of the user to activate the one or more fluid pumps; one or more cameras positioned at the first end portion of the insertion tube; memory positioned within the elongate controller housing; one or more antennas positioned within the elongate controller housing; one or more processors positioned within the elongate controller housing, wherein the one or more processors are in operative communication with at least the memory, the one or more cameras, and the one or more antennas, wherein the one or more processors are configured at least to: receive image data from the one or more cameras; and wirelessly send, through the one or more antennas, the image data to a computing device located at a distance from the one or more antennas.

Variation 10 can include the medical scope of variation 9, further comprising: one or more working channels positioned within the insertion tube, the one or more working channels being constructed and arranged to extend at least from an exterior surface of the elongate controller housing to the first end portion of the insertion tube; wherein at least a first working channel of the one or more working channels is constructed and arranged to receive at least biopsy forceps, grasping forceps, a fulguration electrode, a guide wire, or any combination thereof. The working channel is constructed to allow for external connection to additional devices or tubing using a luer-lock style connection.

Variation 11 can include the medical scope of variation 9, further comprising: one or more batteries constructed and arranged to provide power to at least the one or more fluid pumps, the one or more cameras, and the one or more processors.

Variation 12 can include the medical scope of variation 11, further comprising: one or more light sources positioned at the first end portion of the insertion tube; wherein the one or more batteries are further constructed and arranged to provide power to at least the one or more light sources.

Variation 13 can include the medical scope of variation 9, wherein the first control includes: a lever in mechanical communication with the one or more cables or wires.

Variation 14 can include the medical scope of variation 9, wherein the insertion tube is constructed and arranged to be inserted into a urethra of a patient.

Variation 15 can include the medical scope of variation 9, wherein the insertion tube is constructed and arranged to be inserted into an esophagus of a patient.

Variation 16 can include the medical scope of variation 9, wherein the medical scope is a cystoscope, bronchoscope, a hysteroscope, a vaginoscope, or a colonoscope.

According to variation 17, a medical scope can include a handheld controller constructed and arranged to be operated in a one hand mode of operation and in a two hand mode of operation, the handheld controller including: an elongate controller housing sized to be operable by one hand of a user; a first control proximate to a first side of the elongate controller housing; a second control proximate to a second side opposite the first side of the elongate controller housing; an insertion tube constructed and arranged to be connected to the elongate controller housing, wherein at least a first end portion of the insertion tube is constructed and arranged to be deflected; one or more cables or wires positioned within the insertion tube, the one or more cables or wires being constructed and arranged to connect at least the first control to the first end portion of the insertion tube, wherein during the one hand mode of operation the first control is positioned so as to be actuated by one thumb of the user to tension at least a first cable or wire of the one or more cables or wires to deflect at least the first end portion of the insertion tube; one or more irrigation channels positioned within the insertion tube, the one or more irrigation channels being constructed and arranged to extend at least from inside the housing to the first end portion of the insertion tube; a fluid reservoir positioned within the elongate controller housing and including a fluid cavity that is constructed and arranged to be in fluid communication with at least a first irrigation channel of the one or more irrigation channels positioned inside the insertion tube; one or more fluid pumps in operative communication with the second control and constructed and arranged to be in fluid communication with the fluid cavity, the one or more fluid pumps being constructed and arranged to pump fluid from the fluid reservoir and into the one or more irrigation channels, wherein during the one hand mode of operation the second control is positioned so as to be actuated by one or more fingers of the user to activate the one or more fluid pumps; one or more cameras positioned at the first end portion of the insertion tube; memory positioned within the elongate controller housing; one or more antennas positioned within the elongate controller housing; one or more processors positioned within the elongate controller housing, wherein the one or more processors are in operative communication with at least the memory, the one or more cameras, and the one or more antennas, wherein the one or more processors are configured at least to: receive video data from the one or more cameras; and wirelessly send, through the one or more antennas, the video data to a computing device located at a distance from the one or more antennas.

Variation 18 can include the medical scope of variation 17, further comprising: one or more working channels positioned within the insertion tube, the one or more working channels being constructed and arranged to extend at least from an exterior surface of the elongate controller housing to the first end portion of the insertion tube; wherein at least a first working channel of the one or more working channels is constructed and arranged to receive at least biopsy forceps, grasping forceps, a fulguration electrode, a guide wire, or any combination thereof.

Variation 19 can include the medical scope of variation 17, further comprising: one or more batteries constructed and arranged to provide power to at least the one or more fluid pumps, the one or more cameras, and the one or more processors.

Variation 20 can include the medical scope of variation 19, further comprising: one or more light sources positioned at the first end portion of the insertion tube; wherein the one or more batteries are further constructed and arranged to provide power to at least the one or more light sources.

Many different embodiments have been disclosed herein, in connection with the above description and the drawings. It will be understood that it would be unduly repetitious and obfuscating to describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

An equivalent substitution of two or more elements can be made for anyone of the elements in the claims below or that a single element can be substituted for two or more elements in a claim. Although elements can be described above as acting in certain combinations, and even initially claimed as such, it is to be expressly understood that one or more elements from a claimed combination can, in some cases, be excised from the combination and that the claimed combination can be directed to a subcombination or variation of a subcombination.

It will be appreciated by persons skilled in the art that the present embodiment is not limited to what has been particularly shown and described hereinabove. A variety of modifications and variations are possible considering the above teachings without departing from the following claims.

What is claimed is:

1. A medical scope, comprising:

a handheld controller constructed and arranged to be operated in a one hand mode of operation and in a two hand mode of operation, the handheld controller including:

an elongate controller housing sized to be operable by one hand of a user;

a first control proximate to a first side of the elongate controller housing;

a second control proximate to a second side opposite the first side of the elongate controller housing;

an insertion tube constructed and arranged to be connected to the elongate controller housing, wherein at least a first end portion of the insertion tube is constructed and arranged to be deflected;

one or more cables or wires positioned within the insertion tube, the one or more cables or wires being constructed and arranged to connect at least the first control to the first end portion of the insertion tube, wherein during the one hand mode of operation the first control is positioned so as to be actuated by one thumb of the user to tension at least a first cable or wire of the one or more cables or wires to deflect at least the first end portion of the insertion tube;

one or more irrigation channels positioned within the insertion tube, the one or more irrigation channels being constructed and arranged to extend at least from inside the housing to the first end portion of the insertion tube;

a fluid reservoir positioned within the elongate controller housing and including a fluid cavity that is constructed and arranged to be in fluid communication with at least a first irrigation channel of the one or more irrigation channels positioned inside the insertion tube;

one or more fluid pumps in operative communication with the second control and constructed and arranged to be in fluid communication with the fluid cavity, the one or more fluid pumps being constructed and arranged to pump fluid from the fluid reservoir and into the one or more irrigation channels, wherein during the one hand mode of operation the second control is positioned so as to be actuated by one or more fingers of the user to activate the one or more fluid pumps;

one or more cameras positioned at the first end portion of the insertion tube;

memory positioned within the elongate controller housing;

one or more antennas positioned within the elongate controller housing;

one or more processors positioned within the elongate controller housing, wherein the one or more processors are in operative communication with at least the memory, the one or more cameras, and the one or more antennas, wherein the one or more processors are configured at least to:

receive image data from the one or more cameras; and wirelessly send, through the one or more antennas, the image data to a computing device located within a predetermined distance from the one or more antennas.

2. The medical scope of claim 1, further comprising:

one or more working channels positioned within the insertion tube, the one or more working channels being constructed and arranged to extend at least from an exterior surface of the elongate controller housing to the first end portion of the insertion tube;

wherein at least a first working channel of the one or more working channels is constructed and arranged to receive at least biopsy forceps, grasping forceps, a fulguration electrode, a guide wire, or any combination thereof.

3. The medical scope of claim 1, further comprising:

one or more batteries constructed and arranged to provide power to at least the one or more fluid pumps, the one or more cameras, and the one or more processors.

4. The medical scope of claim 3, further comprising:

one or more light sources positioned at the first end portion of the insertion tube; wherein the one or more batteries are further constructed and arranged to provide power to at least the one or more light sources.

5. The medical scope of claim 1, wherein the first control includes:

a lever in mechanical communication with the one or more cables or wires.

6. The medical scope of claim 1, wherein the insertion tube is constructed and arranged to be inserted into a urethra of a patient.

7. The medical scope of claim 1, wherein the insertion tube is constructed and arranged to be inserted into an esophagus of a patient.

8. The medical scope of claim 1, wherein the medical scope is a cystoscope, bronchoscope, a hysteroscope, a vaginoscope, or a colonoscope.

9. A medical scope, comprising:

a handheld controller constructed and arranged to be operated in a one hand mode of operation and in a two hand mode of operation, the handheld controller including:

an elongate controller housing sized to be operable by one hand of a user;

a first control proximate to a first side of the elongate controller housing;

a second control proximate to a second side opposite the first side of the elongate controller housing;

an insertion tube constructed and arranged to be connected to the elongate controller housing, wherein at least a first end portion of the insertion tube is constructed and arranged to be deflected;

one or more cables or wires positioned within the insertion tube, the one or more cables or wires being constructed and arranged to connect at least the first control to the first end portion of the insertion tube, wherein during the one hand mode of operation the first control is positioned so as to be actuated by one thumb of the user to tension at least a first cable or wire of the one or more cables or wires to deflect at least the first end portion of the insertion tube;

one or more irrigation channels positioned within the insertion tube, the one or more irrigation channels being constructed and arranged to extend at least from inside the housing to the first end portion of the insertion tube;

a fluid reservoir positioned within the elongate controller housing and including a fluid cavity that is constructed and arranged to be in fluid communication with at least a first irrigation channel of the one or more irrigation channels positioned inside the insertion tube;

one or more fluid pumps in operative communication with the second control and constructed and arranged to be in fluid communication with the fluid cavity, the one or more fluid pumps being constructed and arranged to pump fluid from the fluid reservoir and into the one or more irrigation channels, wherein during the one hand mode of operation the second control is positioned so as to be actuated by one or more fingers of the user to activate the one or more fluid pumps;

one or more cameras positioned at the first end portion of the insertion tube;

memory positioned within the elongate controller housing;

one or more antennas positioned within the elongate controller housing;

one or more processors positioned within the elongate controller housing, wherein the one or more processors are in operative communication with at least the memory, the one or more cameras, and the one or more antennas, wherein the one or more processors are configured at least to:

receive image data from the one or more cameras; and wirelessly send, through the one or more antennas, the image data to a computing device located at a distance from the one or more antennas.

10. The medical scope of claim 9, further comprising:

one or more working channels positioned within the insertion tube, the one or more working channels being constructed and arranged to extend at least from an exterior surface of the elongate controller housing to the first end portion of the insertion tube;

wherein at least a first working channel of the one or more working channels is constructed and arranged to receive at least biopsy forceps, grasping forceps, a fulguration electrode, a guide wire, or any combination thereof.

11. The medical scope of claim 9, further comprising:

one or more batteries constructed and arranged to provide power to at least the one or more fluid pumps, the one or more cameras, and the one or more processors.

12. The medical scope of claim 11, further comprising:

one or more light sources positioned at the first end portion of the insertion tube; wherein the one or more batteries are further constructed and arranged to provide power to at least the one or more light sources.

13. The medical scope of claim 9, wherein the first control includes:

a lever in mechanical communication with the one or more cables or wires.

14. The medical scope of claim 9, wherein the insertion tube is constructed and arranged to be inserted into a urethra of a patient.

15. The medical scope of claim 9, wherein the insertion tube is constructed and arranged to be inserted into an esophagus of a patient.

16. The medical scope of claim 9, wherein the medical scope is a cystoscope, bronchoscope, a hysteroscope, a vaginoscope, or a colonoscope.

17. A medical scope, comprising:

a handheld controller constructed and arranged to be operated in a one hand mode of operation and in a two hand mode of operation, the handheld controller including:

an elongate controller housing sized to be operable by one hand of a user;

a first control proximate to a first side of the elongate controller housing;

a second control proximate to a second side opposite the first side of the elongate controller housing;

an insertion tube constructed and arranged to be connected to the elongate controller housing, wherein at least a first end portion of the insertion tube is constructed and arranged to be deflected;

one or more cables or wires positioned within the insertion tube, the one or more cables or wires being constructed and arranged to connect at least the first control to the first end portion of the insertion tube, wherein during the one hand mode of operation the first control is positioned so as to be actuated by one thumb of the user to tension at least a first cable or wire of the one or more cables or wires to deflect at least the first end portion of the insertion tube;

one or more irrigation channels positioned within the insertion tube, the one or more irrigation channels being constructed and arranged to extend at least from inside the housing to the first end portion of the insertion tube;

a fluid reservoir positioned within the elongate controller housing and including a fluid cavity that is constructed and arranged to be in fluid communication with at least a first irrigation channel of the one or more irrigation channels positioned inside the insertion tube;

one or more fluid pumps in operative communication with the second control and constructed and arranged to be in fluid communication with the fluid cavity, the one or more fluid pumps being constructed and arranged to pump fluid from the fluid reservoir and into the one or more irrigation channels, wherein during the one hand mode of operation the second control is positioned so as to be actuated by one or more fingers of the user to activate the one or more fluid pumps;

one or more cameras positioned at the first end portion of the insertion tube;

memory positioned within the elongate controller housing;

one or more antennas positioned within the elongate controller housing;

one or more processors positioned within the elongate controller housing, wherein the one or more processors are in operative communication with at least the memory, the one or more cameras, and the one or more antennas, wherein the one or more processors are configured at least to:

receive video data from the one or more cameras; and wirelessly send, through the one or more antennas, the video data to a computing device located at a distance from the one or more antennas.

18. The medical scope of claim 17, further comprising:

one or more working channels positioned within the insertion tube, the one or more working channels being constructed and arranged to extend at least from an exterior surface of the elongate controller housing to the first end portion of the insertion tube;

wherein at least a first working channel of the one or more working channels is constructed and arranged to receive at least biopsy forceps, grasping forceps, a fulguration electrode, a guide wire, or any combination thereof.

19. The medical scope of claim 17, further comprising:

one or more batteries constructed and arranged to provide power to at least the one or more fluid pumps, the one or more cameras, and the one or more processors.

20. The medical scope of claim 19, further comprising:

one or more light sources positioned at the first end portion of the insertion tube; wherein the one or more batteries are further constructed and arranged to provide power to at least the one or more light sources.

* * * * *